US012751733B2

(12) United States Patent
Takami

(10) Patent No.: US 12,751,733 B2
(45) Date of Patent: Oct. 6, 2026

(54) ENERGY TREATMENT APPARATUS

(71) Applicant: OLYMPUS MEDICAL SYSTEMS CORP., Tokyo (JP)

(72) Inventor: Sadayoshi Takami, Hachioji (JP)

(73) Assignee: OLYMPUS MEDICAL SYSTEMS CORP., Tokyo (JP)

(*) Notice: Subject to any disclaimer, the term of this patent is extended or adjusted under 35 U.S.C. 154(b) by 273 days.

(21) Appl. No.: 18/416,238

(22) Filed: Jan. 18, 2024

(65) Prior Publication Data

US 2024/0156485 A1 May 16, 2024

Related U.S. Application Data

(63) Continuation of application No. PCT/JP2021/027548, filed on Jul. 26, 2021.

(51) Int. Cl.
*A61B 17/32* (2006.01)
*A61B 17/00* (2006.01)

(52) U.S. Cl.
CPC ................. *A61B 17/320092* (2013.01); *A61B 2017/00026* (2013.01); *A61B 2017/320093* (2017.08)

(58) Field of Classification Search
CPC .. A61B 17/320092; A61B 2017/00026; A61B 2017/320093; A61B 18/1206; A61B 18/1445; A61B 2018/00875; A61B 2018/00994; A61B 18/12
See application file for complete search history.

(56) References Cited

U.S. PATENT DOCUMENTS

| | | | |
|---|---|---|---|
| 2016/0256190 | A1 | 9/2016 | Tsubuku |
| 2018/0333182 | A1 | 11/2018 | Clauda |
| 2018/0333185 | A1 | 11/2018 | Asher et al. |
| 2018/0333187 | A1 | 11/2018 | Sawhney |
| 2018/0333188 | A1 | 11/2018 | Nott et al. |

(Continued)

FOREIGN PATENT DOCUMENTS

| | | | |
|---|---|---|---|
| JP | 2020520721 | A | 7/2020 |
| JP | 2020520726 | A | 7/2020 |

(Continued)

OTHER PUBLICATIONS

2018073915_translated (Year: 2018).*

(Continued)

*Primary Examiner* — Adam Z Minchella
*Assistant Examiner* — Ashleigh Lauren Kern
(74) *Attorney, Agent, or Firm* — Schwegman Lundberg & Woessner, P.A.

(57) ABSTRACT

An energy treatment apparatus includes: a first power source configured to supply power by which a transducer generates an ultrasonic vibration; a second power source configured to supply a high frequency current and a high frequency voltage to a first grasping piece and a second grasping piece; a first detecting circuit configured to detect an electrical characteristic relating to the power supplied to the transducer over time; a second detecting circuit configured to detect the high frequency current and the high frequency voltage supplied to a portion between the first grasping piece and the second grasping piece over time; and a processor configured to control the first power source and the second power source.

18 Claims, 10 Drawing Sheets

(56) References Cited

U.S. PATENT DOCUMENTS

| | | | |
|---|---|---|---|
| 2018/0333189 | A1 | 11/2018 | Asher et al. |
| 2018/0333190 | A1 | 11/2018 | Krumm et al. |
| 2019/0150974 | A1 | 5/2019 | Tsubuku et al. |
| 2019/0239920 | A1 | 8/2019 | Kawasaki |
| 2021/0322090 | A1 | 10/2021 | Takami et al. |
| 2022/0079652 | A1 | 3/2022 | Legaspi et al. |
| 2022/0202465 | A1 | 6/2022 | Nott et al. |
| 2022/0202466 | A1 | 6/2022 | Clauda |

FOREIGN PATENT DOCUMENTS

| | | | | |
|---|---|---|---|---|
| WO | WO-2015122309 | A1 | 8/2015 | |
| WO | WO-2018020578 | A1 | 2/2018 | |
| WO | WO-2018073915 | A1 * | 4/2018 | ..... A61B 17/320092 |
| WO | WO-2020148837 | A1 * | 7/2020 | ......... A61B 18/1445 |
| WO | WO-2020240799 | A1 | 12/2020 | |

OTHER PUBLICATIONS

2020148837_translated (Year: 2020).*
WO_2018073915_A1 (Year: 2018).*
WO_2020148837_A1 (Year: 2020).*
"International Application Serial No. PCT/JP2021/027548, International Search Report dated Sep. 7, 2021", w/ English Translation, (Sep. 7, 2021), 4 pgs.

* cited by examiner

ENERGY TREATMENT APPARATUS

CROSS-REFERENCE TO RELATED APPLICATIONS

This application is a continuation of International Application No. PCT/JP2021/027548, filed on Jul. 26, 2021, the entire contents of which are incorporated herein by reference.

BACKGROUND

1. Technical Field

The present disclosure relates to an energy treatment apparatus.

2. Related Art

In the related art, an energy treatment system that performs coagulation and incision of a living tissue by applying a treatment energy to the living tissue has been known (for example, refer to International Publication Pamphlet No. WO2015/122309).

In the energy treatment system described in International Publication Pamphlet No. WO2015/122309, an ultrasonic energy is adopted as the treatment energy. Specifically, the energy treatment system includes a treatment tool and a control device described below.

The treatment tool includes an ultrasonic transducer that generates ultrasonic vibrations by an electric power from the control device, and a first and a second grasping pieces described below.

The first grasping piece transmits the ultrasonic vibrations, and applies the ultrasonic vibrations to a living tissue. In other words, it treats the living tissue by applying an ultrasonic energy to the living tissue.

The second grasping piece catches a living tissue between itself and the first grasping piece.

The control device includes a power source that outputs an electric power to generate ultrasonic vibrations, a detecting circuit that detects an ultrasonic impedance value of the ultrasonic transducer, and a processor that controls an operation of the power source.

When a living tissue is incised by using an ultrasonic energy, it is common that stop of output of the ultrasonic energy is dependent on the operation of a user. Accordingly, when completion of incision of the living tissue is not clear because it is difficult to confirm it visually, or the like, the output of the ultrasonic energy can be continued unnecessarily. In such a case, because the output of the ultrasonic energy is continued in a state in which the first grasping piece abuts on the second grasping piece, wear of the second grasping piece is concerned.

In the energy treatment system described in International Publication Pamphlet No. WO2015/122309, by monitoring the behavior of ultrasonic impedance value, completion of incision of a living tissue is determined.

SUMMARY

In some embodiments, an energy treatment apparatus includes: a first power source configured to supply power by which a transducer generates an ultrasonic vibration; a second power source configured to supply a high frequency current and a high frequency voltage to a first grasping piece and a second grasping piece; a first detecting circuit configured to detect an electrical characteristic relating to the power supplied to the transducer over time; a second detecting circuit configured to detect the high frequency current and the high frequency voltage supplied to a portion between the first grasping piece and the second grasping piece over time; and a processor configured to control the first power source and the second power source. The processor is configured to determine, based on a result of tissue discrimination of a treatment target, a treatment state of the treatment target by either a method of determining whether the electrical characteristic detected by the first detecting circuit exceeds a predetermined value, or a method of determining both of whether the electrical characteristic detected by the first detecting circuit exceeds a predetermined value and whether a variation of a phase difference of the high frequency voltage and the high frequency current detected by the second detecting circuit is in a converged state.

The above and other features, advantages and technical and industrial significance of this disclosure will be better understood by reading the following detailed description of presently preferred embodiments of the disclosure, when considered in connection with the accompanying drawings.

DETAILED DESCRIPTION

Hereinafter, forms (hereinafter, embodiments) to implement the disclosure will be explained with reference to the drawings. The embodiments explained below are not intended to limit the disclosure. Furthermore, in description of the drawings, identical reference symbols are assigned to identical components.

First Embodiment

Schematic Configuration of Energy Treatment System

Figure 1:
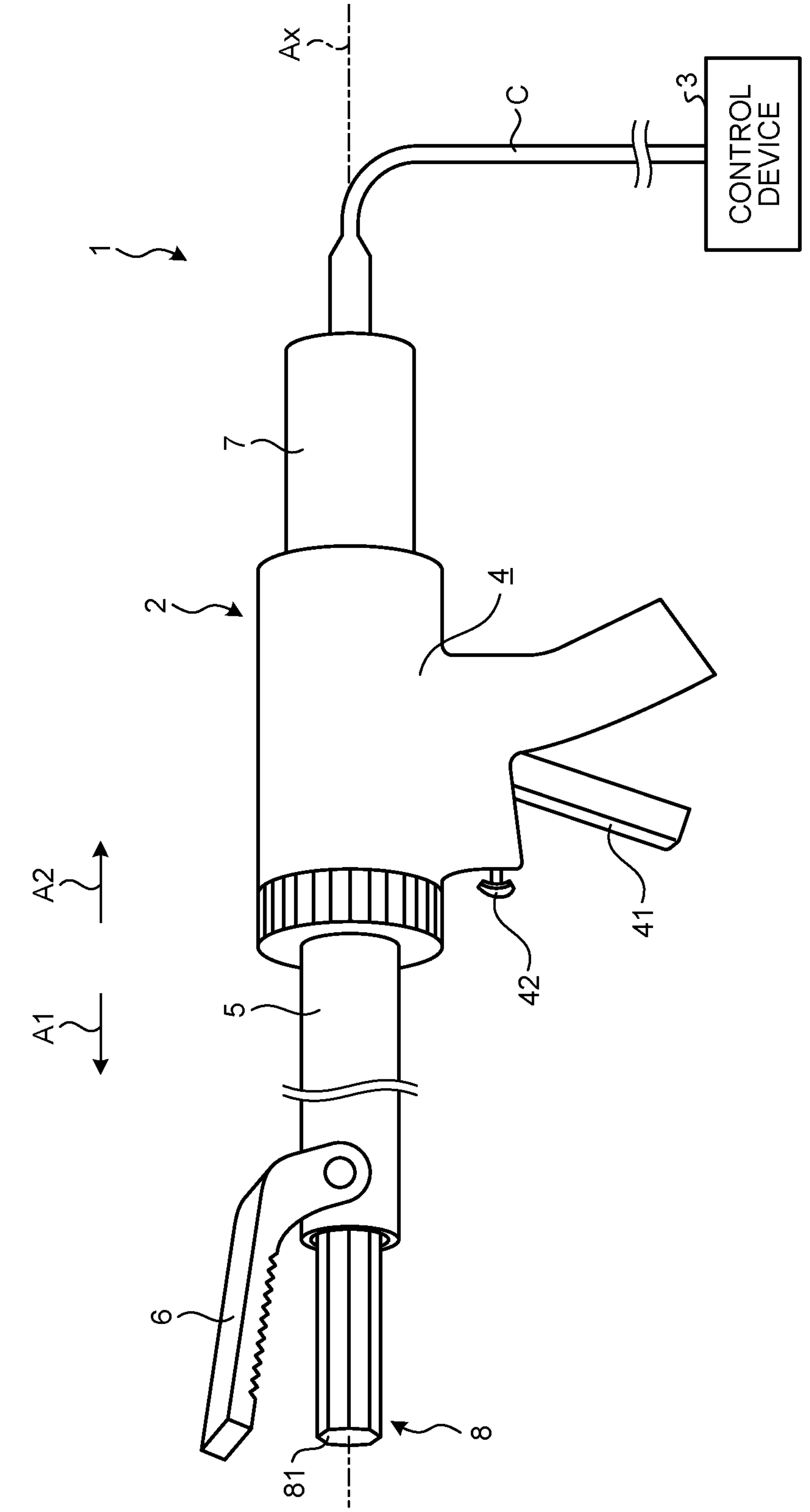
FIG. 1 is a diagram illustrating an energy treatment system according to a first embodiment.

FIG. 1 is a diagram illustrating an energy treatment system 1 according to a first embodiment.

The energy treatment system 1 applies a treatment energy to an area to be a target of treatment in a living tissue (hereinafter, denoted as target area), and thereby treats the target area. In the first embodiment, as the treatment energy, an ultrasonic energy and a high frequency energy are used.

The treatment means, for example, coagulation and incision of a target area. This energy treatment system 1 includes, as illustrated in FIG. 1, a treatment tool 2 and a control device 3.

The treatment tool 2 is an ultrasonic treatment tool that uses a bolt-tightened Langevin-type transducer (BLT) to treat a target area through an abdominal wall. This treatment tool 2 includes, as illustrated in FIG. 1, a handle 4, a sheath 5, a jaw 6, a transducer unit 7, and a vibration transmitting portion 8.

The handle 4 is a portion grabbed by an operator with a hand. In this handle 4, an operating knob 41 and an operating button 42 are arranged as illustrated in FIG. 1.

The sheath 5 has a cylindrical shape. In the following, the center axis of the sheath 5 is denoted as a center axis Ax (FIG. 1). Moreover, in the following, one side along the center axis Ax is denoted as a distal end side A1 (FIG. 1), and the other side is denoted as a proximal end side A2 (FIG. 1). The sheath 5 is attached to the handle 4 as a part on the proximal end side A2 is inserted inside the handle 4 from the distal end side A1 of the handle 4.

Figure 2:
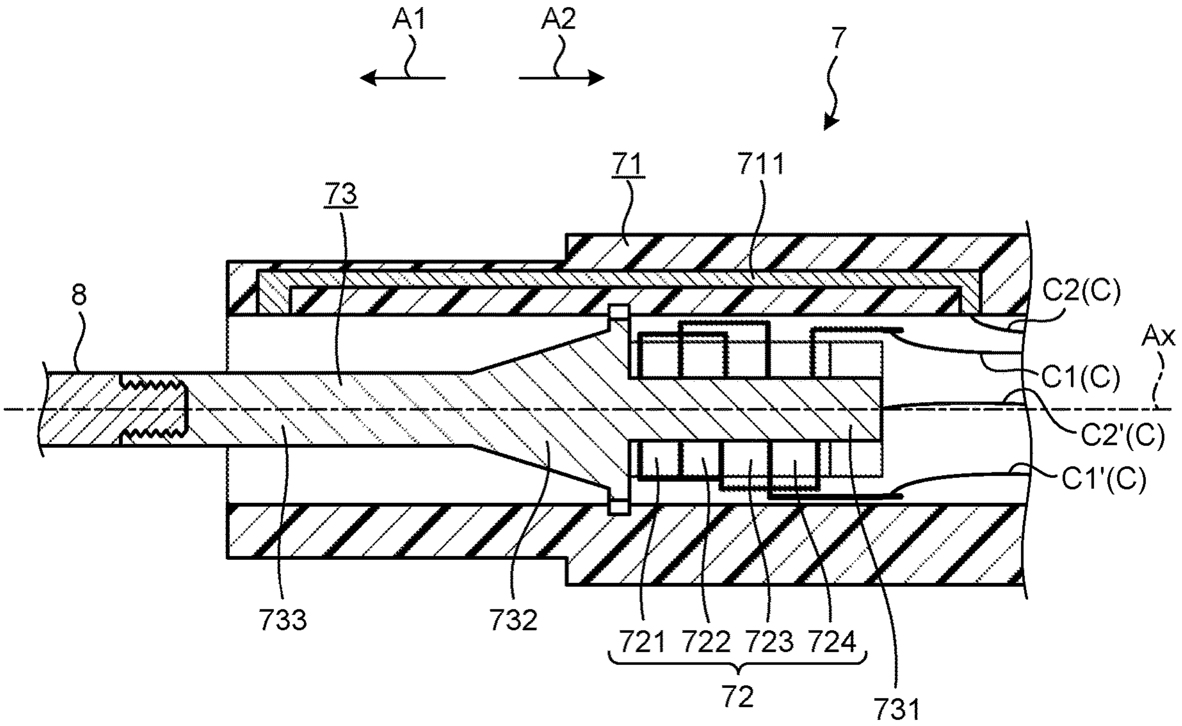
FIG. 2 is a diagram illustrating a transducer unit.

FIG. 2 is a cross-section illustrating the transducer unit 7. Specifically, FIG. 2 is a cross-section of the transducer unit 7 cut along a plane including the center axis Ax. The transducer unit 7 includes a transducer case 71, an ultrasonic transducer 72, and a horn 73 as illustrated in FIG. 2.

The transducer case 71 extends linearly along the center axis Ax, and is attached to the handle 4 as a portion on the distal end side A1 is inserted inside the handle 4 from the proximal end side A2 of the handle 4. When the transducer case 71 is attached to the handle 4, an end portion on the distal end side A1 is connected to an end portion on the proximal end side in the sheath 5.

The ultrasonic transducer 72 is housed inside the transducer case 71, and generates ultrasonic vibrations under the control of the control device 3. In the first embodiment, the ultrasonic vibrations are the BLT having multiple piezoelectric devices 721 to 724 stacked along the center axis Ax. In the first embodiment, the piezoelectric device is constituted of four pieces of the piezoelectric devices 721 to 724, but the number is not limited to four and can be any other number.

The horn 73 is housed inside the transducer case 71, and amplifies the ultrasonic vibrations generated by the ultrasonic transducer 72. This horn 73 has a long shape linearly extending along the center axis Ax. This horn 73 has a configuration in which a first mounting portion 731, a cross-sectional-area varying portion 732, and a second mounting portion 733 aligned from the proximal end side A2 to the distal end side A1 as illustrated in FIG. 2.

The first mounting portion 731 is a portion on which the ultrasonic transducer 72 is mounted.

The cross-sectional-area varying portion 732 is a portion having a shape in which the cross-sectional area decreases as it approaches the distal end side A1, and that amplifies the ultrasonic vibrations.

The second mounting portion 733 is a portion on which the vibration transmitting portion 8 is mounted.

The jaw 6 and the vibration transmitting portion 8 grasps a target area, and applies an ultrasonic energy and a high-frequency energy to the target area to thereby treat the target area.

Specifically, the jaw 6 is constituted of an electrically conductive material, such as metal, and is rotatably attached to an end portion on the distal end side A1 in the sheath 5. The jaw 6 corresponds to a second grasping piece, and grasps a target area between a treating portion 81 (FIG. 1) constituting the vibration transmitting portion 8 and itself.

Although specific illustration is omitted, an opening closing mechanism that opens and closes the jaw 6 relative to the treating portion 81 according to an operation of the operating knob 41 by an operator is arranged inside the handle 4 and the sheath 5 described above. Moreover, in the jaw 6, a resin pad is attached on a surface opposing to the treating portion 81. Because this pad has the electrical insulation property, it has a function of preventing a short circuit between the jaw 6 and the vibration transmitting portion 8. Furthermore, the pad has a function of preventing breakage of the vibration transmitting portion 8 vibrating with ultrasonic waves by colliding with the jaw 6 when incision of a target area by ultrasonic vibrations is completed.

The vibration transmitting portion 8 is constituted of an electrically conductive material, such as metal, and has a long shape extending linearly along the center axis Ax. This vibration transmitting portion 8 is inserted inside the sheath 5 in a state in which a portion on the distal end side A1 protrudes outside as illustrated in FIG. 1. Moreover, an end portion of the vibration transmitting portion 8 on the proximal end side A2 is connected to the second mounting portion 733 as illustrated in FIG. 2. The vibration transmitting portion 8 transmits ultrasonic vibrations that have been generated by the ultrasonic transducer 72 and that have passed through the horn 73 from the proximal end side A2 to the end portion on the distal end side A1, and applies the ultrasonic vibrations to a target area grasped between the end portion on the distal end side A1 and the jaw 6, to thereby treat the target area. That is, the target area is treated by an ultrasonic energy being applied from the end portion on the distal end side A1.

In this vibration transmitting portion 8, the end portion on the distal end side A1 functions as the treating portion 81 (FIG. 1) to treat a target area in a state in which the target area is grasped between itself and the jaw 6. This vibration transmitting portion 8 corresponds to a first grasping piece.

The control device 3 is electrically connected to the treatment tool 2 by an electric cable C (FIG. 1), and comprehensively controls the operation of the treatment tool 2.

A detailed configuration of the control device 3 will be explained in "Configuration of Control Device" described later.

Configuration of Control Device

Next, a configuration of the control device 3 will be explained.

Figure 3:
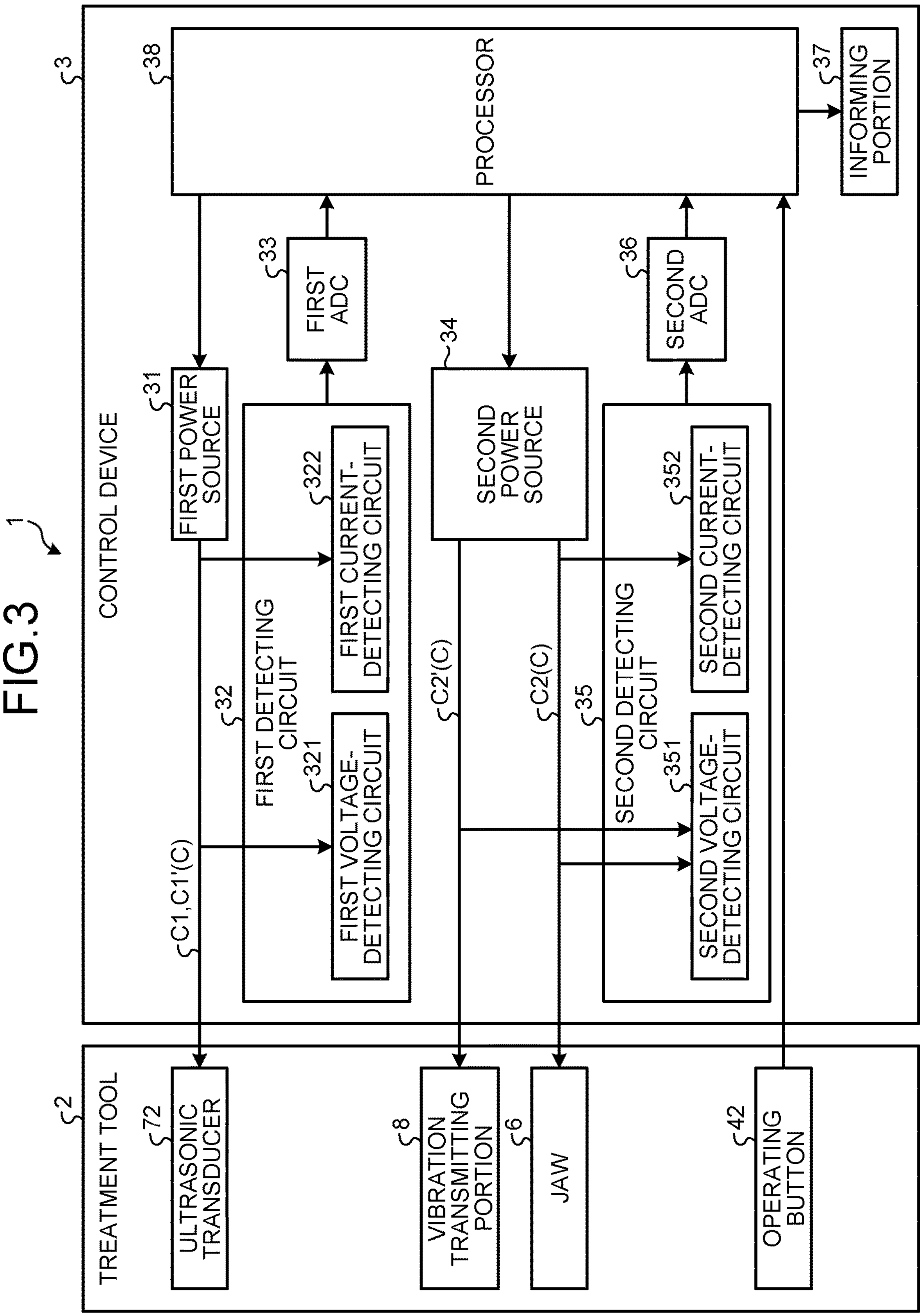
FIG. 3 is a block diagram illustrating a configuration of a control device.

FIG. 3 is a block diagram illustrating a configuration of the control device 3.

The control device 3 includes a first power source 31, a first detecting circuit 32, a first analog-to-digital converter (ADC) 33, a second power source 34, a second detecting circuit 35, a second ADC 36, an informing portion 37, and a processor 38 as illustrated in FIG. 3.

To the ultrasonic transducer 72, as illustrated in FIG. 2, a pair of transducer lead wires C1, C1' constituting an electric cable C are connected. In FIG. 3, for convenience of explanation, the pair of transducer lead wires C1, C1' are illustrated as a single line.

The first power source 31 outputs a driving signal that is an electric power to generate ultrasonic vibrations to the ultrasonic transducer 72 through the pair of transducer lead wires C1, C1' under control of the processor 38. Thus, the ultrasonic transducer 72 generates ultrasonic vibrations.

Hereinafter, for convenience of explanation, the driving signal output from the first power source 31 to the ultrasonic transducer 72 is denoted as an input driving signal, and a signal obtained by modifying the input driving signal by frequency response of the ultrasonic transducer 72 is denoted as output driving signal.

The first detecting circuit 32 includes a first voltage-detecting circuit 321, which is a voltage sensor to detect a voltage value, and a first current-detecting circuit 322, which is an electric current sensor to detect an electric current value, and detects a US signal (analog signal) according to the output driving signal over time. The US signal corresponds to "electrical characteristic value of ultrasonic transducer".

Specifically, for the US signal, a phase signal of voltage in the output driving signal (hereinafter, denoted as US-voltage phase signal), a phase signal of an electric current in the output driving signal (hereinafter, denoted as US-current phase signal), a phase difference between voltage and current in the output driving signal (hereinafter, denoted as US phase difference), an electric current value in the output driving signal (hereinafter, denoted as US current), an impedance value calculated from the US current and the US voltage (hereinafter, denoted as ultrasonic impedance value), and the like can be provided as examples.

The first ADC 33 converts the US signal (analog signal) output from the first detecting circuit 32 into a digital signal. The first ADC 33 outputs the converted US signal (digital signal) to the processor 38.

In the transducer case 71, as illustrated in FIG. 2, a first conductive portion 711 that extends from an end portion on the proximal end side A2 to an end portion on the distal end side A1 is arranged. Moreover, in the sheath 5, although specific illustration is omitted, a second conductive portion that extends from an end portion on the proximal end side A2 to an end portion on the distal end side A1, and that electrically connects the first conductive portion 711 and the jaw 6 is arranged. Furthermore, at the end portion on the proximal end side A2 in the first conductive portion 711, a high-frequency lead wire C2 constituting the electric cable C is connected. Moreover, to the first mounting portion 731, a high-frequency lead wire C2' constituting the electric cable C is connected.

The second power source 34 outputs a high frequency current and a high frequency voltage to a portion between the jaw 6 and the vibration transmitting portion 8 through the pair of high-frequency lead wire C2, C2', the first conductive portion 711, the second conductive portion, and the horn 73 under control of the processor 38. Thus, a high frequency electric current flows through the target area grasped between the jaw 6 and the treating portion 81. That is, to the target area, a high frequency energy is applied. Joule heat is generated in the target area as the high frequency current flows therethrough, and the target area is treated.

As described above, the vibration transmitting portion 8 corresponds to a first electrode. Moreover, the jaw 6 corresponds to a second electrode.

The second detecting circuit 35 includes a second voltage-detecting circuit 351 that is a voltage sensor to detect a voltage value, and a second current-detecting circuit 352 that is a current sensor to detect a current value, and detects an HF signal according to a high frequency current and a high frequency voltage that are output from the second power source 34 to the jaw 6 and the treating portion 81 over time.

Specifically, for the HF signal, a high frequency electric current (hereinafter, denoted as HF current) and a high frequency voltage (hereinafter, denoted as HF voltage) that are output from the second power source 34 to the jaw 6 and the treating portion 81, a high frequency power calculated from the HF current and the HF voltage (hereinafter, denoted as HF power), an impedance value calculated from the HF current and the HF voltage (hereinafter, denoted as HF impedance value), a phase difference between the HF current and the HF voltage (hereinafter, denoted as HF phase difference), and the like can be provided as examples.

The second ADC 36 converts the HF signal (analog signal) output from the second detecting circuit 35 into a digital signal. The second ADC 36 outputs the converted HF signal (digital signal) to the processor 38.

The informing portion 37 informs predetermined information under control of the processor 38. Examples of this informing portion 37 include, for example, a light emitting diode (LED) that informs predetermined information by illumination, flashing, or a color when illuminated, a display device that displays predetermined information, a speaker that outputs predetermined information by sound, and the like. The informing portion 37 is not necessarily required to be arranged in the control device 3 as illustrated in FIG. 3, but may be arranged in the treatment tool 2.

The processor 38 is constituted of a central processing unit (CPU), a field-programmable gate array (FPGA), or the like, and controls overall operations of the energy treatment system 1 according to a program stored in a memory (not illustrated). Detailed functions of the processor 38 will be explained in "Control Method Performed by Processor" described later.

Control Method Performed by Processor

Next, a control method performed by the processor 38 will be explained.

Figure 4:
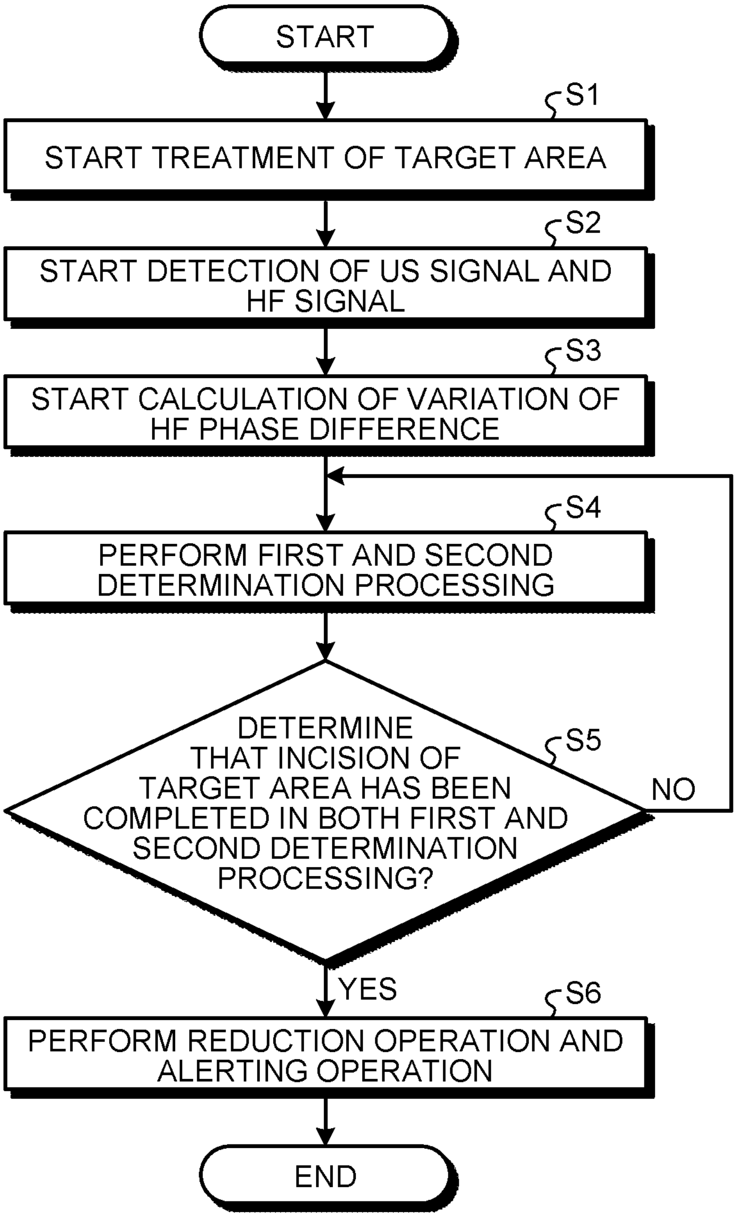
FIG. 4 is a flowchart illustrating a control method performed by a processor.

FIG. 4 is a flowchart illustrating the control method performed by the processor 38.

In the following, for convenience of explanation, a method of determining completion of incision of a target area grasped between the jaw 6 and the treating portion 81 will be mainly explained.

First, the processor 38 starts treatment of a target area that is grasped between the jaw 6 and the treating portion 81 when the operating button 42 is pressed by an operator (step S1). That is, the processor 38 controls operation of the first and the second power sources 31, 34 when the operating button 42 is pressed by an operator, and starts application of an ultrasonic energy and a high frequency energy to the target area.

After step S1, the processor 38 starts detection of the US signal and the HF signal by controlling operation of the first and the second detecting circuits 32, 35 (step S2).

Figure 5:
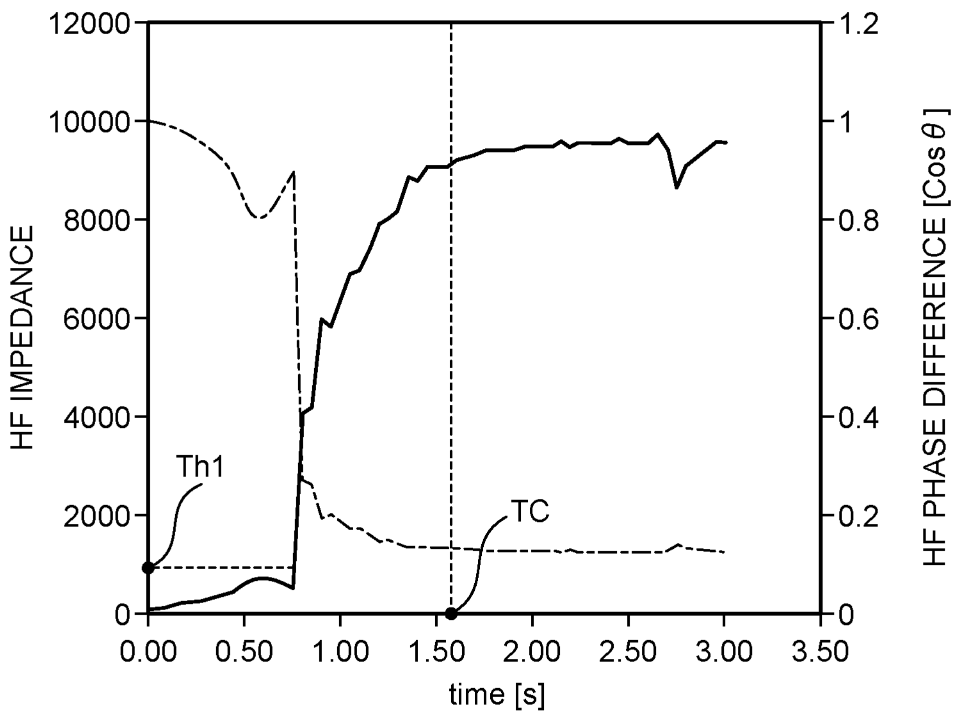
FIG. 5 is a diagram illustrating behaviors of an HF phase difference and an HF impedance value in an HF signal when the control method illustrated in FIG. 4 is performed.

FIG. 5 is a diagram illustrating behaviors of the HF phase difference and the HF impedance value in the HF signal at the time of performing the control method illustrated in FIG. 4. In FIG. 5, the behavior of the HF phase difference is indicated by a single dashed line, and the behavior of the HF impedance value is indicated by a solid line. Moreover, in FIG. 5, the behavior of the HF phase difference is expressed by Case. The HF phase difference described in the following also signifies Case. Furthermore, in FIG. 5, a time TC indicates a time when incision of a target area is completed.

The HF impedance value exhibits a following behavior at an initial stage after the treatment of a target area is started.

Specifically, the HF impedance value gradually decreases, and reaches a minimum value when moisture in the target area reaches a boiling state. Moreover, the HF impedance value returns to increase if treatment of the target area is further continued, because the moisture in the target area evaporates. In FIG. 5, because the order of the vertical axis is high, the behavior of the HF impedance value at the initial stage described above is not adequately indicated.

After the initial stage described above, the HF impedance value increases rapidly as the target area begins to be incised as illustrated in FIG. 5, and then converges.

On the other hand, as illustrated in FIG. 5, when treatment of the target area is started, the HF phase difference gradually decreases from 1 (0°). The HF phase difference rapidly decreases as the target area begins to be incised, and thereafter, converges to zero neighborhood (90° neighborhood).

After step S2, the processor 38 starts calculation of variation of the HF phase difference detected by the second detecting circuit 35 (step S3). FIG. 4 illustrates such that step S3 is performed after step S2 for convenience of explanation, but step S2 and step S3 are performed substantially at the same time in an actual situation.

In the first embodiment, the processor 38 calculates a variance $s^2$ of the HF phase difference as a variation of the HF phase difference. Specifically, the processor 38 calculates the variance $s^2$ of the HF phase difference by Equation 1 below. In Equation 1, n signifies the number of pieces of data of differences (HF phase difference) used to calculate the variance, and is 3 or larger. $x_i$ is a value of each data (HF phase difference).

$$s^2 = \frac{1}{n}\sum_{i=1}^{n}(x_i - \bar{x})^2 \quad (1)$$

$$\bar{x} = \frac{1}{n}\sum_{i=1}^{n} x_i$$

For example, the processor 38 acquires 10 HF phase differences detected every 50 ms for a duration of 500 ms, and calculates a variance $s^2$ of the HF phase difference by Equation 1 using the 10 HF phase differences. That is, when a time at a current point is 500 ms, the processor 38 calculates the variance $s^2$ of the HF phase difference at the current point of time (500 ms) by Equation 1 using the 10 HF phase differences including an HF phase difference at 50 ms (n=1), an HF phase difference at 100 ms (n=2), . . . , and an HF phase difference at 500 ms (N=10). Moreover, when a time at a current point is 550 ms, the processor 38 calculates the variance $s^2$ of the HF phase difference at the current point of time (550 ms) by Equation 1 using 10 HF phase differences including an HF phase difference at 100 ms (n=1), an HF phase difference at 150 ms (n=2), . . . , and an HF phase difference at 550 ms (N=10). n is not limited to 10, and may be any number as long as it is 3 or more. Furthermore, a sampling cycle of the HF phase difference to be used when calculating the variance $s^2$ of the HF phase difference is not limited to 50 ms, and may be other cycles.

After step S3, the processor 38 performs the first and the second determination processing (step S4).

Figure 6:
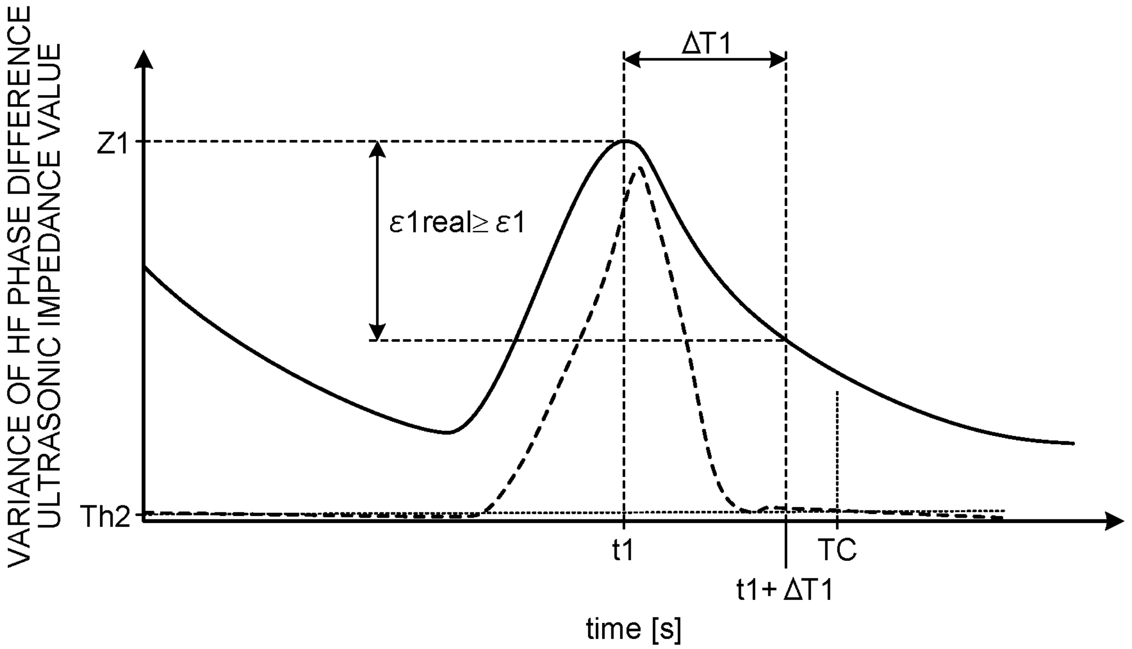
FIG. 6 is a diagram explaining a first and a second determination processing.

FIG. 6 is a diagram explaining the first and the second determination processing. Specifically, FIG. 6 is a diagram illustrating behaviors of the ultrasonic impedance value and the variance $s^2$ of the HF phase difference at the time of performing the control method illustrated in FIG. 4. In FIG. 6, the behavior of the ultrasonic impedance value is indicated by a solid line, and the behavior of the variance $s^2$ of the HF phase difference is indicated by a single dashed line.

Specifically, the processor 38 performs the first determination processing as described below.

The ultrasonic impedance value being the US signal varies according to a load on the vibration transmitting portion 8, in other words, on a load on the ultrasonic transducer 72 connected to the vibration transmitting portion 8. Specifically, a pressing force from the jaw 6 to the treating portion 81 gradually increases along with a change in the state of a target area between the jaw 6 and the treating portion 81 or the like since the treatment of the target area is started. Therefore, the load on the vibration transmitting portion 8 also increases gradually, and the ultrasonic impedance value also increases gradually over time as illustrated in FIG. 6. To gradually increase over time means that the ultrasonic impedance value gradually increases as time progresses, and it also includes the ultrasonic impedance value gradually increases with minute fluctuations within several tens of Ω or less.

At a time in the vicinity of the time TC when the incision is completed (for example, at a time t1 in FIG. 6), because the jaw 6 is positioned close to the treating portion 81, a surface of the pad arranged on the jaw 6 changes in structure due to friction heat generated by ultrasonic vibrations of the treating portion 81. Therefore, the load on the vibration transmitting portion 8 gradually decreases, and the ultrasonic impedance value also gradually decreases over time from the time t1 as illustrated in FIG. 6. To gradually decrease over time means that the ultrasonic impedance value gradually decreases as time processes, and it also includes that the ultrasonic impedance value gradually decreases with minute fluctuations within several tens of Ω or less. That is, the ultrasonic impedance value peaks at the time t1.

The processor 38 first detects a gradual-decrease start time (time t1 in FIG. 6) at which the ultrasonic impedance value starts decreasing gradually in the first determination processing (hereinafter, denoted as provisional peak-detection processing). Moreover, the processor 38 stores an ultrasonic impedance value Z1 (FIG. 6) at the gradual-decrease start time in a memory (not illustrated) as a provisional peak value.

Next, the processor 38 calculates a difference ε1real between an ultrasonic impedance value at a time t1+ΔT1 when predetermined reference time ΔT1 has passed since the gradual-decrease start time t1 and the provisional peak value (ultrasonic impedance value Z1) stored in the memory.

Next, the processor 38 determines whether the difference ε1real is equal to or higher than a predetermined threshold ε1.

When it is determined that the difference ε1real is equal to or higher than the predetermined threshold ε1, the processor 38 recognizes the provisional peak value detected at the gradual-decrease start time t1 is a peak originated from completion of incision of the target area, and determines that the incision of the target area has been completed in the first determination processing.

On the other hand, when it is determined that the difference ε1real is lower than the predetermined threshold ε1, the processor 38 recognizes that the provisional peak detected at the gradual-decrease start time t1 is not a peak originated from completion of incision of the target area, and returns to the provisional peak-detection processing described above again.

"Predetermined condition" is a fact that an ultrasonic impedance value has decreased by the threshold ε1 or more when the predetermined time ΔT1 has elapsed since the time t1 at which the ultrasonic impedance value had started gradual decrease. That is, the threshold ε1 corresponds to a first threshold.

Moreover, the processor 38 performs the second determination processing as described below.

The variance $s^2$ of the HF phase difference rapidly increases as the target area begins to be incised as illustrated in FIG. 6, and rapidly decreases as it comes close to completion of incision of the target area, and converges thereafter.

The processor 38 first monitors whether the HF impedance value being the HF signal exceeds a threshold Th1 (FIG. 5) all the time in the second determination processing.

Next, when it is determined that the HF impedance value exceeds the threshold Th1, the processor 38 compares the variance $s^2$ of the HF phase difference and a threshold Th2 (FIG. 6), and thereby monitors whether the variance of the HF phase difference has become a converged state all the time (hereinafter, denoted as convergence monitoring processing). In the first embodiment, the processor 38 determines that it has become the converged state when the variance $s^2$ of the HF phase difference is equal to or lower than the threshold Th2.

When it is determined that the variance $s^2$ of the HF phase difference has become the converged state, the processor 38 determines that incision of the target area has completed in the second determination processing.

On the other hand, when it is determined that the variance $s^2$ of the HF phase difference has not become the converged state, the processor 38 continues the convergence monitoring processing described above When it is determined that incision of the target area has been completed in both the first and the second determination processing (step S5: YES), the processor 38 performs reduction operation and alerting operation described below (step S6). Thereafter, the processor 38 completes this control flow.

The processor 38 performs the reduction operation to reduce the output of power (driving signal) from the first power source 31 to the ultrasonic transducer 72, and the output of the high frequency current and the high frequency voltage from the second power source 34 to the jaw 6 and the vibration transmitting portion 8 at step S6. In the first embodiment, the processor 38 performs the reduction operation to stop operation of the first and the second power sources 31, 34, that is, to stop the output from the first power source 31 to the ultrasonic transducer 72, and the output from the second power source 34 to the jaw 6 and the vibration transmitting portion 8.

Moreover, the processor 38 performs the alerting operation to cause the informing portion 37 to inform the information indicating that incision of the target area has been completed at step S6.

According to the first embodiment explained above, following effects are produced.

In the first determination processing that is incision completion determination of a target area by using an ultrasonic impedance value, while the determination accuracy in the incision completion determination is relatively high when the target area is thin (when the target area is small in size), the determination accuracy in the incision completion determination is relatively low when the target area is thick (when the target area is large in size). On the other hand, in the second determination processing that is incision completion determination of a target area by using a variation of an HF phase difference, the determination accuracy in the incision completion determination is relatively high when the target area is thick (when the target area is large in size).

In the energy treatment system 1 according to the first embodiment, the processor 38 performs the reduction operation when it is determined that incision of a target area has been completed in both the first and the second determination processing.

Therefore, for a target area in which the accuracy of the incision completion determination is relatively low in the first determination processing, it can be compensated for by the accuracy in the incision completion determination in the second processing, and it is possible to support varies types of target areas, and to detect completion of incision of the target areas accurately.

In the energy treatment system 1 according to the first embodiment, the processor 38 performs the alerting operation besides the reduction operation when it is determined that incision of a target area has been completed in both the first and the second determination processing. Therefore, it is also possible to let an operator or the like recognize the completion of incision of the target area clearly.

Second Embodiment

Next, a second embodiment will be explained.

In the following explanation, identical reference symbols are assigned to identical components to those in the first embodiment described above, and detailed explanation thereof will be omitted or simplified.

Figure 7:
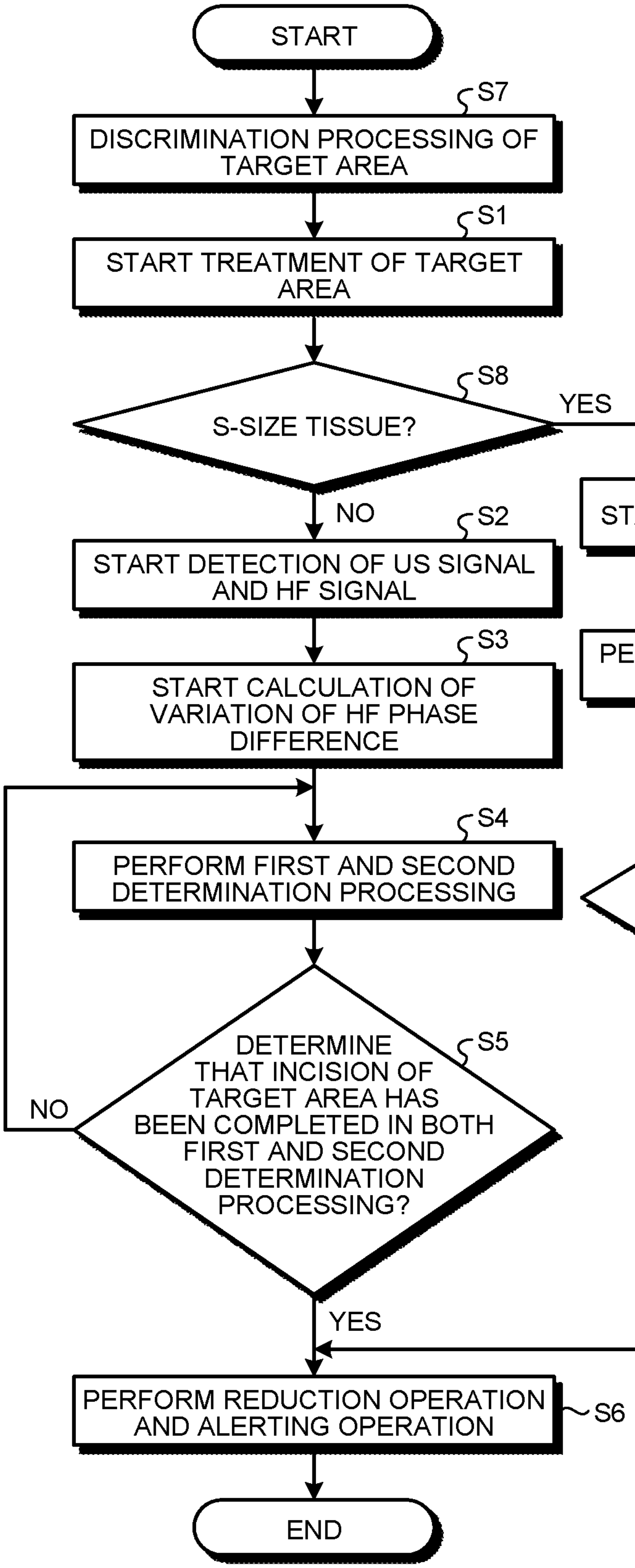
FIG. 7 is a flowchart illustrating a control method performed by a processor according to a second embodiment.

FIG. 7 is a flowchart illustrating a control method performed by the processor 38 according to the second embodiment.

In the second embodiment, as illustrated in FIG. 7, the control method performed by the processor 38 is changed from the first embodiment described above.

In the control method performed by the processor 38 according to the second embodiment, as illustrated in FIG. 7, steps S7 to S11 are added to the control method (FIG. 4) explained in the first embodiment described above. Accordingly, in the following, only steps S7 to S11 will be explained.

Step S7 is performed before step S1.

At step S7, when the operating button 42 is pressed by an operator, the processor 38 performs discrimination processing of a target area that is grasped between the jaw 6 and the treating portion 81 as described below.

Specifically, the processor 38 outputs a constant power to the jaw 6 and the vibration transmitting portion 8 for predetermined time (for example 100 [msec]) by controlling the operation of the second power source 34. The constant power is an amount of power that does not cause thermal modification of the target area.

Next, while making the second power source 34 output the constant power described above to the jaw 6 and the vibration transmitting portion 8, the processor 38 sequentially stores HF impedance values that are HF signals detected by the second detecting circuit 35 in a memory (not illustrated). Moreover, the processor 38 calculates an initial impedance value by averaging the HF impedance values stored in the memory (not illustrated) sequentially in the last period (for example, 20 [msec]) in the predetermined time described above.

Initial impedance values differ between an S-size tissue that is small in size and an L-size tissue that is large in size among target areas. For example, an initial impedance value of the S-size tissue is to be a smaller value than a predetermined discrimination threshold. On the other hand, an initial impedance value of the L-size tissue is to be a larger value than the discrimination threshold.

The processor 38 performs discrimination processing to discriminate a target area grasped between the jaw 6 and the treating portion 81 between the S-size tissue or the L-size tissue by comparing the calculated initial impedance and the discrimination threshold.

Step S8 is performed after step S1.

Specifically, the processor 38 determines whether the target area grasped between the jaw 6 and the treating portion 81 is discriminated as the S-size tissue in the discrimination processing at step S7.

When it has been discriminated as the L-size tissue (step S8: NO), the processor 38 performs steps S2 to S6 sequentially. That is, when it has been discriminated as the L-size tissue (step S8: NO), the processor 38 selects the second determination method in which the first and the second determination processing (step S4) are both performed.

On the other hand, when it has been discriminated as the S-size tissue (step S8: YES), the processor 38 controls operation of the first detecting circuit 32 to start detection of the US signal (step S9), and performs the first determination processing (step S10). That is, when it has been discriminated as the S-size tissue (step S8: YES), the processor 38 selects the first determination processing in which only the first determination processing is performed (step S10).

Furthermore, when it is determined that incision of the target area has been completed (step S11: YES) only by the first determination processing, the processor 38 shifts to step S6.

According to the second embodiment explained above, effects similar to those of the first embodiment described above are produced.

In the energy treatment system 1 according to the second embodiment, the processor 38 changes the determination processing to perform the reduction operation based on a detection result by the second detecting circuit 35. Specifically, the processor 38 determines whether a target area is the L-size tissue or the S-size tissue based on the initial impedance value. The processor 38 performs both the first and the second determination processing when it is the L-size tissue, and performs only the first determination processing when it is the S-size tissue.

That is, because it is possible to perform only the first determination processing for the S-size tissue for which determination accuracy of incision completion determination is relatively high in the first determination processing, it is not necessary to perform the second determination processing for the S-size tissue. Therefore, processing load on the processor 38 can be reduced.

Third Embodiment

Next, a third embodiment will be explained.

In the following explanation, identical reference symbols are assigned to identical components to those in the second embodiment described above, and detailed explanation thereof will be omitted or simplified.

Figure 8:
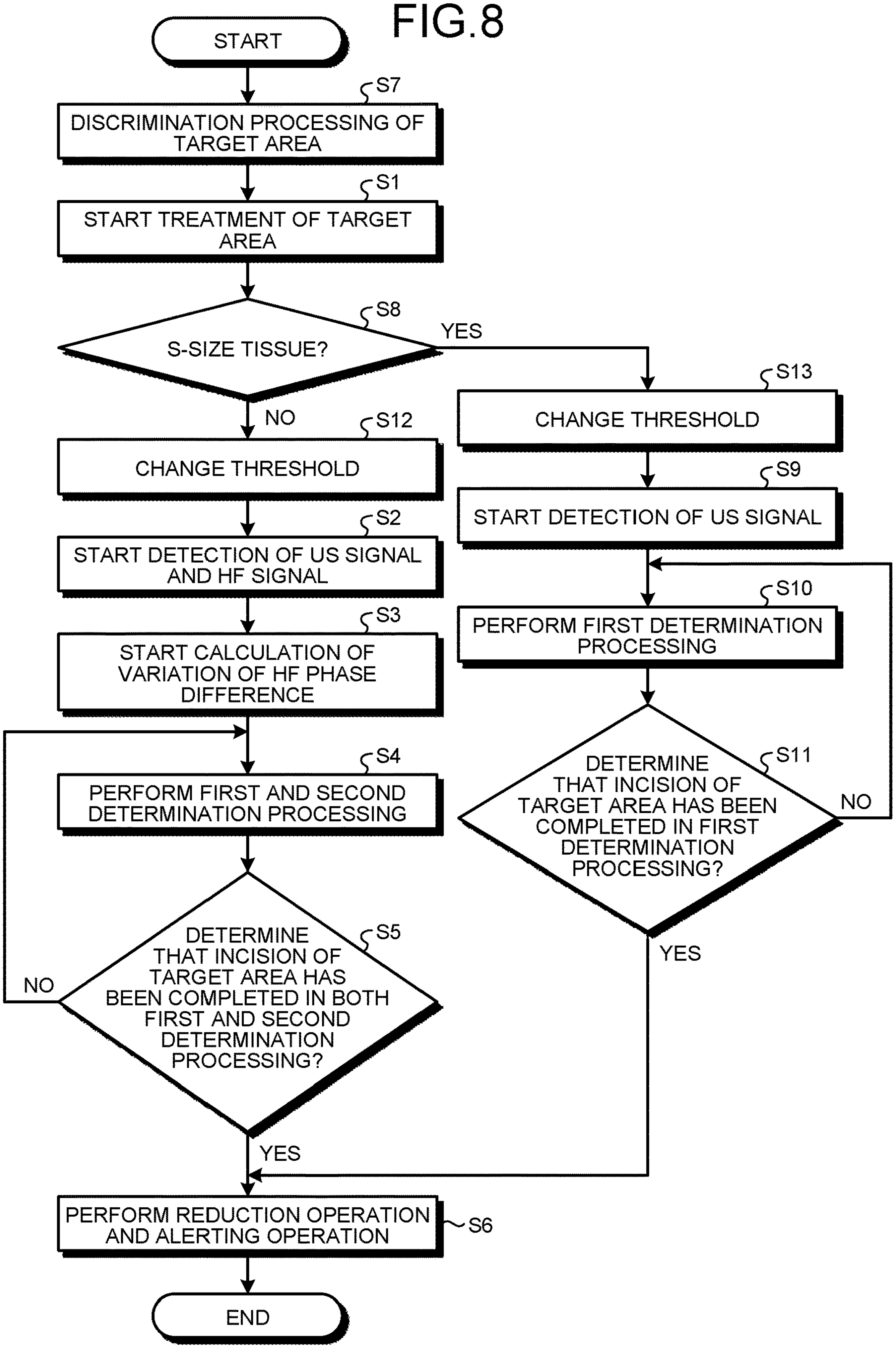
FIG. 8 is a flowchart illustrating a control method performed by a processor according to a third embodiment.

FIG. 8 is a flowchart illustrating a control method performed by the processor 38 according to the third embodiment.

In the third embodiment, as illustrated in FIG. 8, the control method performed by the processor 38 is changed from the second embodiment described above.

In the control method performed by the processor 38 according to the third embodiment, as illustrated in FIG. 8, steps S12 and S13 are added to the control method (FIG. 7) explained in the second embodiment described above. Accordingly, in the following, only steps S12 and S13 will be explained.

Steps S12 and S13 are performed when it is discriminated as the L-size tissue (step S8: NO), and when it is discriminated as the S-size tissue (step S8: YES), respectively.

At step S12, The processor 38 changes the first threshold used in the first determination processing to a value according to the L-size tissue. On the other hand, at step S13, the processor 38 changes the first threshold used in the first determination processing to a value according to the S-size tissue.

The first threshold corresponds to the threshold ε1 and the predetermined time ΔT1.

Figure 9:
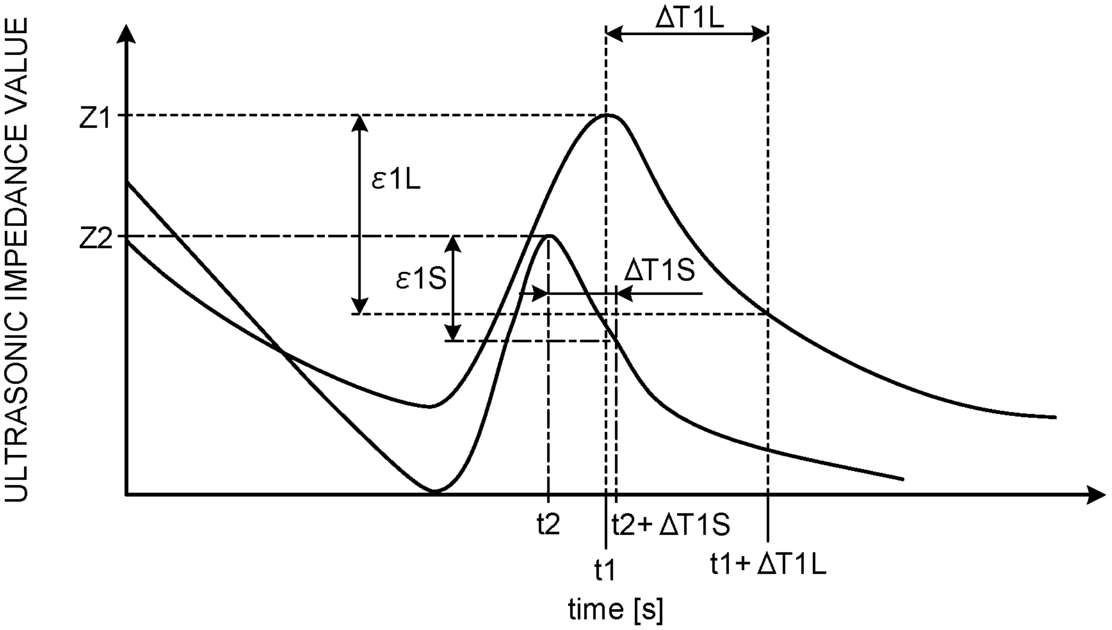
FIG. 9 is a diagram explaining steps S12, S13.

FIG. 9 is a diagram explaining steps S12, S13. Specifically, FIG. 9 is a diagram corresponding to FIG. 6. In FIG. 9, a behavior of the ultrasonic impedance value when the target area is the L-size tissue is indicated by a solid line, and a behavior of the ultrasonic impedance value when the target area is the S-size tissue is indicated by a single dashed line.

Specifically, when it has been discriminated as the L-size tissue (step S8: NO), the processor 38 sets the threshold ε1 to threshold ε1L (FIG. 9) according to the L-size tissue, and sets the reference time ΔT1 to reference time ΔT1L (FIG. 9) according to the L-size tissue at step S12.

On the other hand, when it has been discriminated as the S-size tissue (step S8: YES), the processor 38 sets the threshold ε1 to a threshold ε1S (FIG. 9) according to the S-size tissue, and sets the reference time ΔT1 to reference time ΔT1S (FIG. 9) according to the S-size tissue at step S13.

The threshold ε1L is a larger value than the threshold ε1S. Moreover, the reference time ΔT1L is a larger value than the reference time ΔT1S.

According to the third embodiment explained above, effects similar to those of the second embodiment described above are produced.

Because the S-size tissue has a small amount of tissue, the peak of the ultrasonic impedance value (ultrasonic impedance value Z2 (FIG. 9)) is low, and it is cut and separated quickly after the peak. On the other hand, for the L-size tissue, there is a possibility that a thin skin still remains even after the peak of the ultrasonic impedance value.

In the energy treatment system 1 according to the third embodiment, the processor 38 changes the first threshold to be used in the first determination processing based on a detection result by the second detecting circuit 35. Specifically, when it has been discriminated as the S-size tissue (step S8: YES), the processor 38 sets the threshold ε1 and the reference time ΔT1 to the threshold ε1S and the reference time ΔT1S, respectively. On the other hand, when it has been discriminated as the L-size tissue (step S8: NO), the processor 38 sets the threshold ε1 and the reference time ΔT1 to the threshold ε1L and the reference time ΔT1L, respectively.

Therefore, when the target area is the S-size tissue, the incision determination can be performed after the reference time ΔT1S has passed since the time t2 at which the ultrasonic impedance value starts to decrease gradually, and it is not necessary to wait unnecessarily long until the incision of the target area is completed. On the other hand, when the target area is the L-size tissue, the incision determination can be performed after the reference time ΔT1L has passed since the time t1 at which the ultrasonic impedance value starts to decrease gradually, and it is possible to reliably determine that the incision of the target area completed.

Fourth Embodiment

Next, a fourth embodiment will be explained.

In the following explanation, identical reference symbols are assigned to identical components to those of the third embodiment described above, and detailed explanation thereof will be omitted or simplified.

Figure 10:
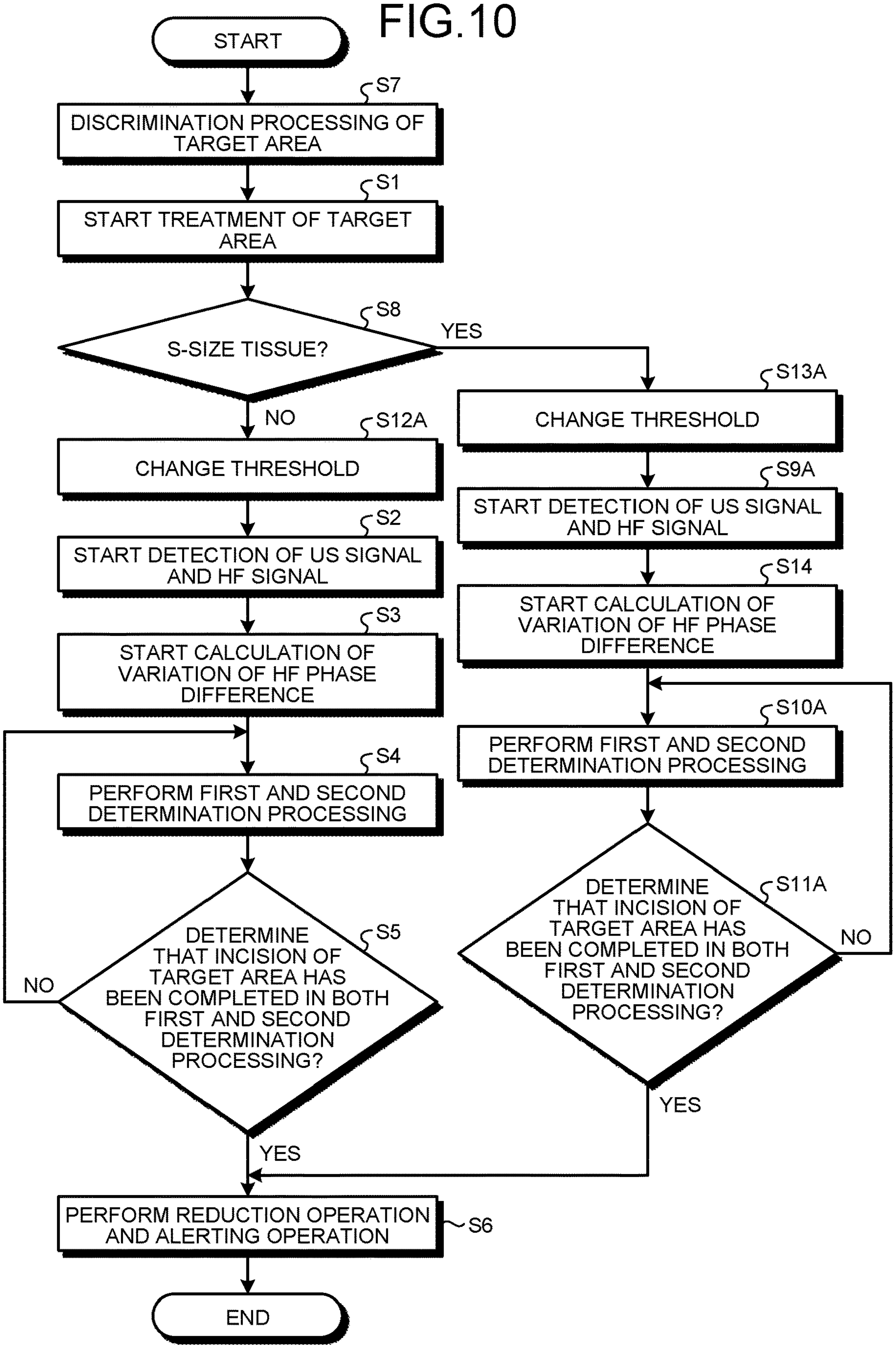
FIG. 10 is a flowchart illustrating a control method performed by a processor according to a fourth embodiment.

FIG. 10 is a flowchart illustrating a control method performed by the processor 38 according to the fourth embodiment.

In the fourth embodiment, as illustrated in FIG. 10, the control method performed by the processor 38 is changed from the third embodiment described above.

In the control method performed by the processor 38 according to the fourth embodiment, as illustrated in FIG. 10, steps S12A, S13A, and S9A to S11A are adopted instead of steps S12, S13, and S9 to S11, and step S14 is added to the control method (FIG. 8) explained in the third embodiment described above. Accordingly, in the following, only steps S12A, S13A, and S9A to S11A, and S14 will be explained.

Figure 11:
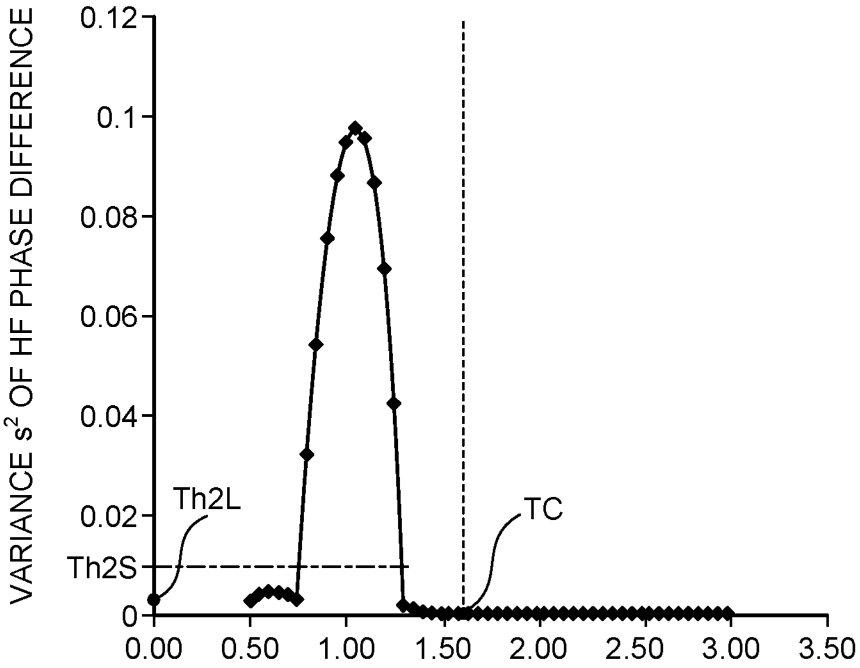
FIG. 11 is a diagram explaining steps S12A, S13A.

FIG. 11 is a diagram explaining steps S12A, S13A. Specifically, FIG. 11 is a diagram corresponding to FIG. 6.

At Step S12A, similarly to the third embodiment described above, the processor 38 changes the first threshold to be used in the first determination processing to a value according to the L-size tissue. Furthermore, the processor 38 changes a second threshold to be used in the second determination processing to a value according to the L-size tissue.

The second threshold is a threshold Th2.

Specifically, when it has been discriminated as the L-size tissue (step S8: NO), similarly to the third embodiment described above, the processor 38 sets the threshold ε1 and the reference time ΔT1 to the threshold ε1L and the reference time ΔT1L, respectively, at step S12A. Furthermore, the processor 38 sets the threshold Th2 to a threshold Th2L (FIG. 11) according to the L-size tissue.

On the other hand, when it has been discriminated as the S-size tissue (step S8: YES), similarly to the third embodiment described above, the processor 38 sets the threshold ε1 and the reference time ΔT1 to the threshold ε1S and the reference time ΔT1S, respectively, at step S13A. Furthermore, the processor 38 sets the threshold Th2 to a threshold Th2S (FIG. 11) according to the S-size tissue.

The threshold Th2S is a value larger than the threshold Th2L as illustrated in FIG. 11.

At step S9A, the processor 38 starts detection of the US signal and the HF signal by controlling operation of the first and the second detecting circuits 32, 35 similarly to step S2.

After step S9A, the processor 38 starts calculation of a variation of the HF phase differences detected by the second detecting circuit 35 (step S14) similarly to step S3.

After step S14, the processor performs both the first and the second determination processing at step S10A similarly to step S4.

After step S10A, the processor 38 determines whether incision of the target area has been completed by both the first and the second determination processing at step S11A similarly to step S5. When it is "NO" at step S11A, step S10A is continued. On the other hand, when it is "YES" at step S11A, it shifts to step S6.

According to the fourth embodiment explained above, effects similar to those of the third embodiment described above are produced.

Because the S-size tissue has a small amount of tissue, as the peak of the variation of the HF phase difference decreases, it is cut and separated quickly after the peak.

In the energy treatment system 1 according to the fourth embodiment, the processor 38 changes the second threshold to be used in the second determination processing based on a detection result by the second detecting circuit 35. Specifically, when it is discriminated as the S-size tissue (step S8: YES), the processor 38 changes it to the threshold Th2 (threshold Th2S) that is large compared to a case in which it is discriminated as the L-size tissue.

Therefore, when a target area is the S-size tissue, it is not necessary to wait unnecessarily long until incision of the target area is completed even when both the first and the second determination processing are adopted.

Other Embodiments

The embodiments to implement the disclosure have so far been explained, but the disclosure is not to be limited to the first to the fourth embodiments described above.

In the first to the fourth embodiments described above, the processor 38 perform the alerting operation besides the reduction operation at step S6, it is not limited thereto, and only the reduction operation may be performed. Moreover, the processor 38 may be performed only the alerting operation at step S6.

In the first to the fourth embodiments described above, the ultrasonic impedance value is adopted as an electrical impedance value of the ultrasonic transducer 72, but it is not limited thereto, and the US phase difference, the US voltage, the US current, or the US power may be adopted.

In the first to the fourth embodiments described above, the variance $s^2$ of the HF phase difference is adopted as a variation of the HF phase difference, but it is not limited thereto, and a standard deviation of the HF phase difference, or a deviation of the HF phase difference may be adopted. The standard deviation of the HF phase difference is a positive square root of the variance $s^2$ of the HF phase difference. Moreover, the deviation of the HF phase difference is calculated by Equation 2 below. In Equation 2, n signifies the number of data (HF phase difference) and is 2 or larger. $x_i$ is a value of each data (HF phase difference).

$$\text{DEVIATION} = x_n - \bar{x} \qquad (2)$$

$$\bar{x} = \frac{1}{n}\sum_{i=1}^{n} x_i$$

In the first to the fourth embodiments described above, the ultrasonic energy and the high frequency energy are adopted as a treatment energy to be applied to a target area, but it is not limited thereto, and a thermal energy may be adopted in addition to the ultrasonic energy and the high frequency energy. "Applying a thermal energy to a target area" means to transmit heat generated in a heater to the target area.

In the first to the fourth embodiments described above, both the ultrasonic energy and the high frequency energy are applied to a target area at step S1, but it is not limited thereto. For example, according to operation of an operator, it may be configured to be switchable between a mode in which only the ultrasonic energy is applied to a target area (hereinafter, denoted as ultrasonic-exclusive mode) and a mode in which both the ultrasonic energy and the high frequency energy are applied to a target area (hereinafter, denoted as combined mode). In this case, in the ultrasonic-exclusive mode, it is preferable that the threshold ε1 be small and the reference time ΔT1 be large. On the other hand, in the combined mode, it is preferable that the threshold ε1 be large and the reference time ΔT1 be small.

In the second to the fourth embodiments, at step S7, the discrimination processing of a target area is performed based on the initial impedance value at step S7, but it is not limited thereto. For example, the discrimination processing of a target area may be performed based on the HF voltage, the HF current, the HF power, or the like.

According to an energy treatment apparatus according to the disclosure, completion of incision of a living tissue can be accurately detected.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An energy treatment apparatus comprising:

a first power source configured to supply power by which a transducer generates an ultrasonic vibration;

a second power source configured to supply a high frequency current and a high frequency voltage to a first grasping piece and a second grasping piece;

a first detecting circuit configured to detect an electrical characteristic relating to the power supplied to the transducer over time;

a second detecting circuit configured to detect the high frequency current and the high frequency voltage supplied to a portion between the first grasping piece and the second grasping piece over time; and a processor configured to control the first power source and the second power source, wherein the processor is configured to determine, based on a result of tissue discrimination of a treatment target, a treatment state of the treatment target by selecting between i) a first method of determining whether the electrical characteristic detected by the first detecting circuit exceeds a predetermined value, or ii) a second method of determining both of whether the electrical characteristic detected by the first detecting circuit exceeds a predetermined value and whether a variation of a phase difference of the high frequency voltage and the high frequency current detected by the second detecting circuit is in a converged state.

2. The energy treatment apparatus according to claim 1, wherein the electrical characteristic is an ultrasonic impedance value that is an electrical impedance value of the transducer.

3. The energy treatment apparatus according to claim 2, wherein the processor is configured to determine that the electrical characteristic has exceeded the predetermined value when a decrease equal to or more than a first threshold is observed after a predetermined time has elapsed since a time at which the ultrasonic impedance value starts to decrease gradually.

4. The energy treatment apparatus according to claim 1, wherein the processor is configured to calculate, as the variation of the phase difference, any one of a deviation, a standard deviation, and a variance of the phase difference.

5. The energy treatment apparatus according to claim 1, wherein the processor is configured to change a determination method to perform a reduction operation to reduce output of at least one of the first power source and the second power source based on a detection result by the second detecting circuit.

6. The energy treatment apparatus according to claim 5, wherein the processor is configured to change a first threshold to be used for determination whether the electrical characteristic has exceeded the predetermined value based on a detection result by the second detecting circuit.

7. The energy treatment apparatus according to claim 5, wherein the processor is configured to change a second threshold to be used for determination whether the variation of the phase difference has become the converged state based on a detection result by the second detecting circuit.

8. The energy treatment apparatus according to claim 1, further comprising:

an informing portion configured to inform predetermined information, wherein the processor is configured to perform an alerting operation to cause the informing portion to inform the predetermined information when it is determined that the electrical characteristic has exceeded the predetermined value and determined that the variation of the phase difference has become the converged state.

9. The energy treatment apparatus according to claim 1, wherein the treatment state of the treatment target is a state of a tissue of the treatment target being cut and separated.

10. The energy treatment apparatus according to claim 1, wherein the processor is configured to reduce or stop output of at least one of the first power source and the second power source after the treatment state of the treatment target is determined.

11. The energy treatment apparatus according to claim 1, wherein the tissue discrimination includes:

causing, prior to treatment of the treatment target, the second power source to output a constant power to the first grasping piece and the second grasping piece for a predetermined time, the constant power being an amount of power that does not cause thermal modification of the treatment target;

acquiring, by the second detecting circuit, a plurality of high-frequency impedance values during the predetermined time;

calculating an initial impedance value using the plurality of high-frequency impedance values in a latter portion of the predetermined time; and discriminating the treatment target based on a comparison between the initial impedance value and a discrimination criterion.

12. The energy treatment apparatus according to claim 11, wherein the processor is configured to:

when the treatment target is discriminated as a first tissue category, determine the treatment state by the first method of determining whether the electrical characteristic detected by the first detecting circuit exceeds the predetermined value without performing the second method of determining whether the variation of the phase difference is in the converged state; and when the treatment target is discriminated as a second tissue category, determine the treatment state by performing both the first method of determining whether the electrical characteristic detected by the first detecting circuit exceeds the predetermined value and the second method of determining whether the variation of the phase difference is in the converged state.

13. The energy treatment apparatus according to claim 12, wherein the processor is configured to change a first threshold and a reference time used for the first method of determining whether the electrical characteristic has exceeded the predetermined value according to whether the treatment target is the first tissue category or the second tissue category.

14. The energy treatment apparatus according to claim 12, wherein the processor is configured to change a second threshold used for determining whether the variation of the phase difference is in the converged state according to whether the treatment target is the first tissue category or the second tissue category.

15. The energy treatment apparatus according to claim 11, wherein the tissue discrimination is performed based on at least one of a high-frequency voltage, a high-frequency current, or a high-frequency power detected by the second detecting circuit.

16. The energy treatment apparatus according to claim 11, wherein the latter portion is 20 milliseconds.

17. The energy treatment apparatus according to claim 11, wherein the predetermined time is 100 milliseconds.

18. The energy treatment apparatus according to claim 11, wherein the predetermined time is 100 milliseconds and the latter portion is 20 milliseconds.

* * * * *